(12) United States Patent
May et al.

(10) Patent No.: US 9,918,753 B2
(45) Date of Patent: Mar. 20, 2018

(54) SPINAL IMPLANT SYSTEM AND METHOD

(71) Applicant: Warsaw Orthopedic, Inc., Warsaw, IN (US)

(72) Inventors: Jason M. May, Cordova, TN (US); Brian A. Butler, Atoka, TN (US); Gary S. Lindemann, Collierville, TN (US); James M. Mirda, Cordova, TN (US); Joshua W. Simpson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 434 days.

(21) Appl. No.: 13/965,949

(22) Filed: Aug. 13, 2013

(65) Prior Publication Data

US 2015/0051648 A1 Feb. 19, 2015

(51) Int. Cl.
*A61B 17/70* (2006.01)

(52) U.S. Cl.
CPC ................ *A61B 17/7086* (2013.01)

(58) Field of Classification Search
CPC ............ A61B 17/7083; A61B 17/7085; A61B 17/7086
See application file for complete search history.

(56) References Cited

U.S. PATENT DOCUMENTS

| 7,160,300 | B2  |    | 1/2007  | Jackson |            |
|-----------|-----|----|---------|---------|------------|
| 7,465,306 | B2  |    | 12/2008 | Pond, Jr. et al. | |
| 7,947,046 | B2  |    | 5/2011  | Justis et al. | |
| 8,002,798 | B2  |    | 8/2011  | Chin et al. | |
| 8,439,924 | B1  | *  | 5/2013  | McBride | ............. A61B 17/708 606/104 |
| 2007/0276867 | A1 |    | 11/2007 | Fishbaine et al. | |
| 2008/0177269 | A1 |    | 7/2008  | Seelig  |            |
| 2011/0022093 | A1 |    | 1/2011  | Sherman et al. | |
| 2013/0018419 | A1 | *  | 1/2013  | Rezach  | ............. A61B 17/7076 606/264 |

* cited by examiner

*Primary Examiner* — Julianna N Harvey

(57) ABSTRACT

An implant support comprises a first portion defining a longitudinal axis and a second portion including at least one arm extending from the first portion. The at least one arm includes a part. An extension is engageable with the at least one arm to move the at least one arm between a first position and a second position such that the part is disposed to releasably engage an implant. A lock is disposed with the first portion and connected with the extension. The lock is biased from a first configuration to a second configuration to engage the first portion and resist disengagement of the at least one arm from the second position. Systems and methods of use are disclosed.

20 Claims, 18 Drawing Sheets

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, an implant support comprises a first portion defining a longitudinal axis and a second portion including at least one arm extending from the first portion. The at least one arm includes a part. An extension is engageable with the at least one arm to move the at least one arm between a first position and a second position such that the part is disposed to releasably engage an implant. A lock is disposed with the first portion and connected with the extension. The lock is biased from a first configuration to a second configuration to engage the first portion and resist disengagement of the at least one arm from the second position.

BRIEF DESCRIPTION OF THE DRAWINGS

The present disclosure will become more readily apparent from the specific description accompanied by the following drawings, in which.

DETAILED DESCRIPTION

Figure 1:
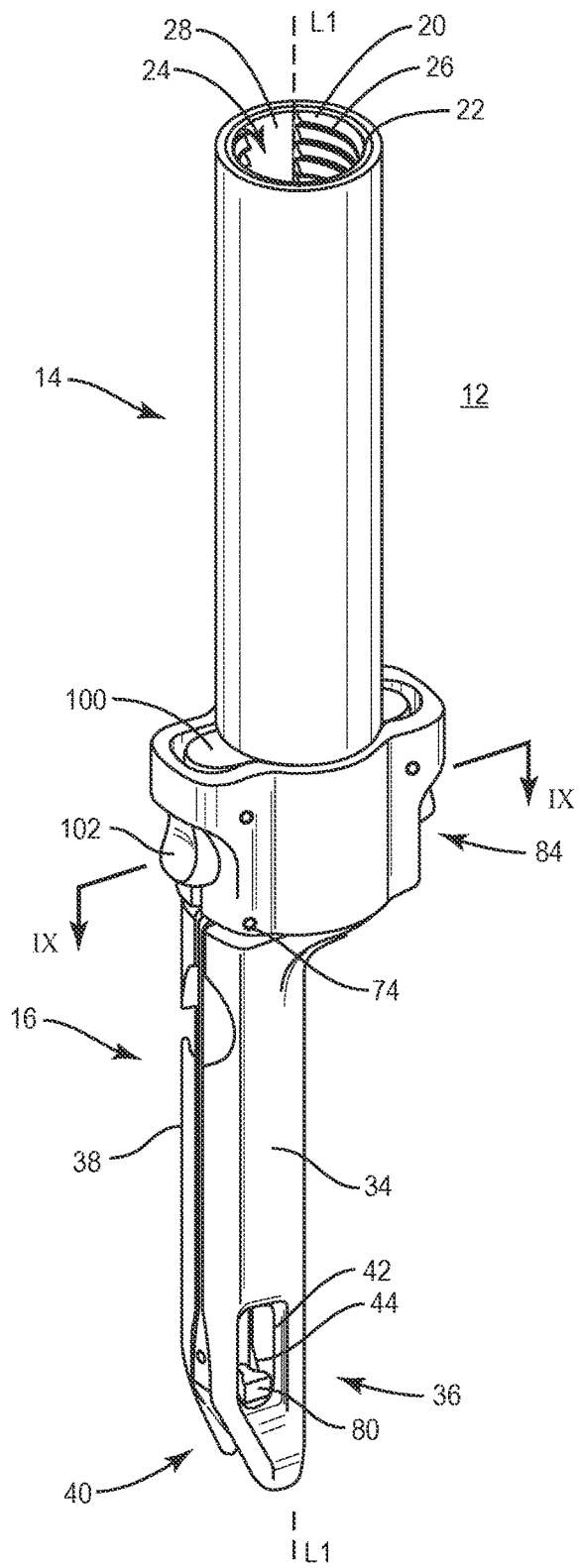
FIG. 1 is a perspective view of components of one embodiment of a system in accordance with the principles of the present disclosure.
Figure 2:
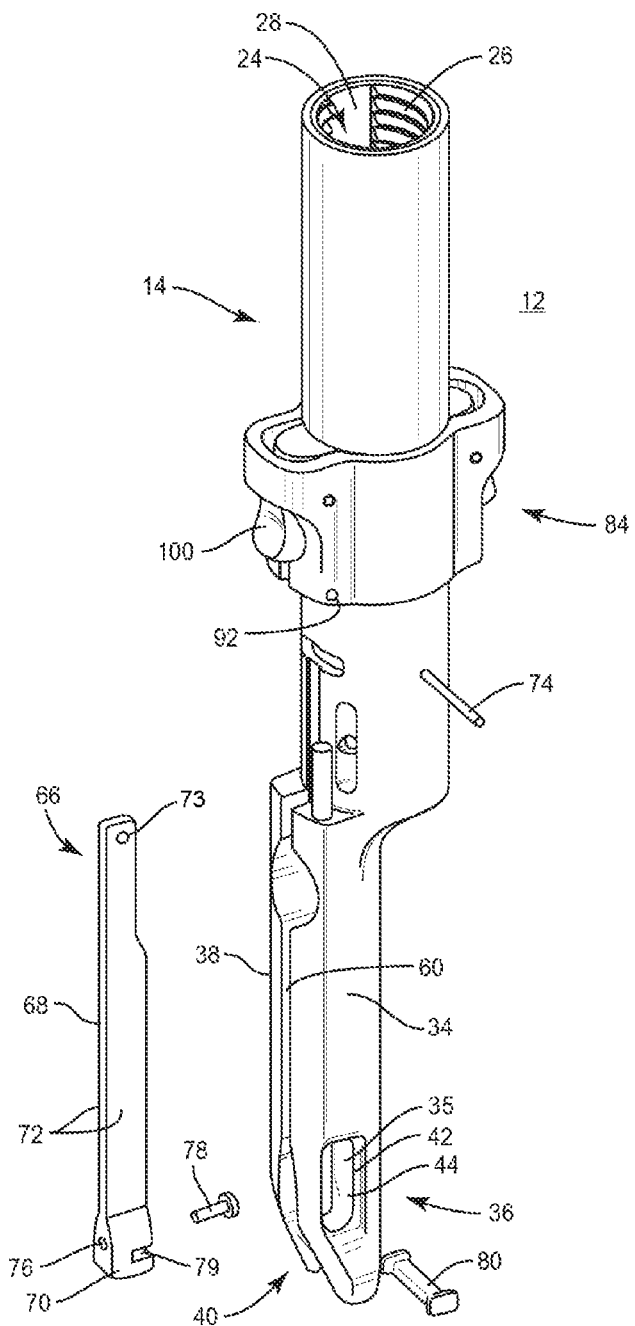
FIG. 2 is a perspective view of components of the system shown in FIG. 1 with parts separated.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. In one embodiment, the system of the present disclosure includes an implant support having a lock for a reduction device. In one embodiment, the lock ensures the engagement of the reduction device to a pedicle screw is not compromised under normal use.

In one embodiment, the lock includes spring loaded buttons that engage recesses or slots in a body of the implant support that connects to an implant. In one embodiment, the lock includes buttons that can be moved from a first position to a second position to selectively engage or disengage the slots. In one embodiment, the lock includes buttons that are housed in a sliding sleeve, which can also be moved from a first position to a second position to actuate engagement and disengagement features to an implant. For example, in a first locked position, the engagement of the buttons into slots of the body prevents translation of a sliding sleeve and prevents unintentional disengagement of the implant system from the implant. In one embodiment, the buttons automatically engage the slots in the body as the sleeve is moved to a locked position.

In one embodiment, the implant support includes a lock having spring tabs formed into the body. In one embodiment, the tabs are biased outwardly from the body and overlap the sliding sleeve. In one embodiment, the sliding sleeve can be moved from a first engaged position to a second disengaged position by depressing the buttons causing movement of the tabs from a first position to a second locked position. In one embodiment, the spring tabs automatically engage to a biased position when released.

In one embodiment, the lock includes a flip lever with a shaft to engage the body. In one embodiment, the lock is turned manually from a first closed position, preventing the sleeve from translating, to a second position, which does not cover the sleeve and allows translation and disengagement from an implant.

In some embodiments, the system may include instruments that are connected or attached to an implant support such as, for example, an extender, a lateral translation handle or derotaton instruments. In one embodiment, the system may have an implant support with a quick release mechanism to allow a reducer to slide into engagement with a spinal rod. In some embodiments, the system can include an implant support having features that prevent a rod and/or a reducer assembly from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-16, there is illustrated components of a surgical system, such as, for example, a spinal implant system 10 in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. In some embodiments, spinal implant system 10 and related methods may be employed with treatments that reduce a spinal rod with the bone fastener using minimally invasive and percutaneous techniques.

Spinal implant system 10 includes an implant support, such as, for example, an extender 12. Extender 12 extends along a longitudinal axis L1 between a first portion, such as, for example, a tubular portion 14 and a second portion, such as, for example, an arm 16. Tubular portion 14 includes a cylindrical cross-section configuration and a proximal opening 20. Portion 14 extends axially from opening 20. In one embodiment, portion 14 may extend from opening 20 in alternate configurations such as, for example, having a radius of curvature, offset and/or staggered. In other embodiments, portion 14 may extend at transverse orientations from opening 20, relative to longitudinal axis L1, for example, perpendicular and/or other angular orientations such as acute or obtuse, co-axial and/or parallel.

Figure 6:
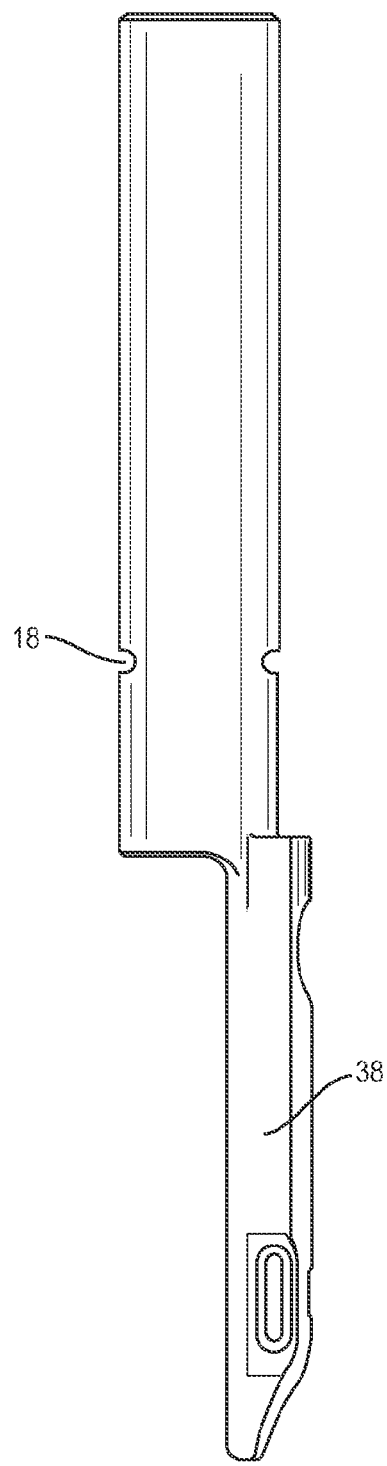
FIG. 6 is a side view of a component of the system shown in FIG. 1.
Figure 7:
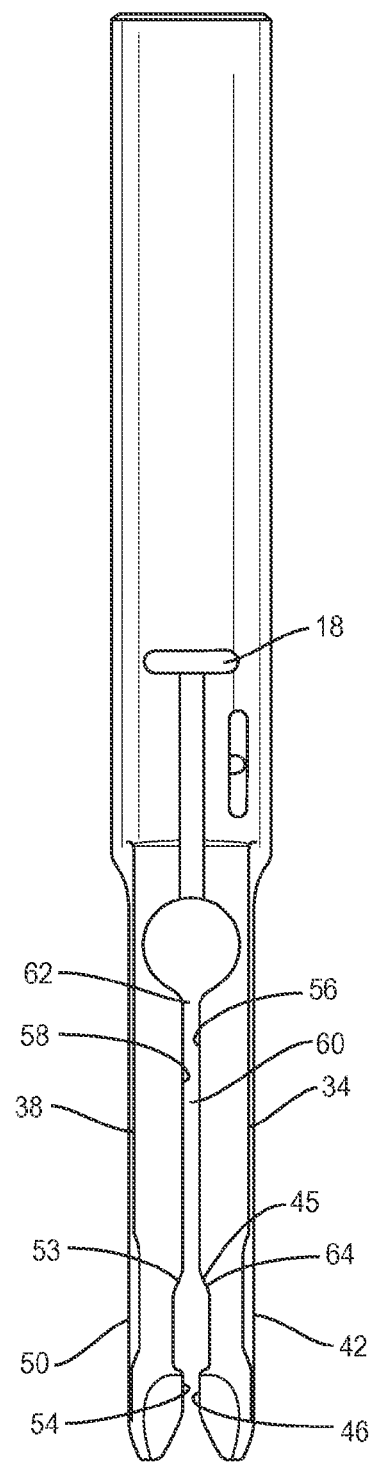
FIG. 7 is a side view of a component of the system shown in FIG. 1.
Figure 8:
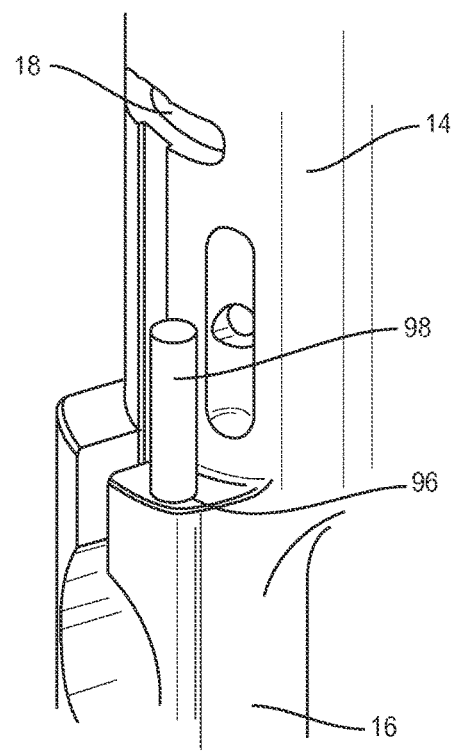
FIG. 8 is a break away perspective view of components of the system shown in FIG. 1.

Portion 14 includes an inner surface 22 that defines an inner cavity, such as, for example, a passageway 24. Inner surface 22 includes a threaded portion 26 and a smooth, non-threaded portion 28. Portions 26, 28 are each configured for engagement with an instrument, as will be described. Portion 14 is configured for disposal of surgical instruments to deliver one or more implants to a surgical site, as will be described. Portion 14 includes an outer surface 30 configured for contact with a passageway 88 of sleeve 84, as discussed herein. A slot 18 is defined between surfaces 22 and 30, as shown in FIGS. 6 and 7. Slot 18 extends transverse to axis L1. Slot 18 is configured to receive a portion of a lock 100, as discussed herein. In one embodiment, slot 18 may extend in alternate configurations such as, for example, having a radius of curvature, offset and/or staggered, perpendicular and/or other angular orientations such as acute or obtuse, co-axial and/or parallel.

In some embodiments, all or only a portion of surfaces 22, 30 may have alternate surface configurations, such as, for example, rough, threaded for connection with surgical instruments, arcuate, undulating, porous, semi-porous, dimpled, polished and/or textured according to the requirements of a particular application. In some embodiments, portion 14 may have alternate cross section configurations, such as, for example, oval, oblong, triangular, rectangular, square, polygonal, irregular, uniform, non-uniform, variable and/or tapered.

Arm 16 extends along axis L1 and extends distally in a linear orientation from portion 14. In some embodiments, arm 16 may extend from portion 14 in alternate configurations such as, for example, transverse, perpendicular and/or other angular orientations such as acute or obtuse, co-axial and/or parallel. Arm 16 includes a first movable leg extension 34 that defines a distal engagement part 36 and a second movable leg extension 38 that defines a distal engagement part 40.

Leg extension 34 includes an inner surface 35 that defines an axial slot 42. Slot 42 includes a tapered track surface 44 configured to guide an actuator 66, as discussed herein. Surface 35 defines a protrusion 46 configured to engage a bone fastener 132, as discussed herein. Leg extension 38 includes an inner surface 48 that defines an axial slot 50. Slot 50 includes a tapered track surface 52 configured to guide actuator 66, as discussed herein. Surface 48 defines a protrusion 54 configured to engage bone fastener 132, as discussed herein. Leg extensions 34, 38 include walls 56, 58, respectively, that are oriented to define an axial arm cavity 60 therebetween. Arm cavity 60 includes a proximal section 62 and a distal section 64 and is configured to receive a surgical instrument.

Leg extensions 34, 38 extend in a cantilevered configuration from portion 14 and are flexible to facilitate movement between a first position, such as, for example, an open position and a second position, such as, for example, a closed position such that protrusions 46, 54 engage fastener 132, as will be described. In one embodiment, extender 12 may include a second arm (not shown) similar to arm 16, which may include one or a plurality of leg extensions (not shown). In some embodiments, leg extensions 34, 38 may extend in alternate configurations and orientations, such as, for example, those alternatives described herein.

Extender 12 includes an extension, such as, for example, an actuator 66 configured for slidable disposal within arm cavity 60. Actuator 66 is axially movable within arm cavity 60 to move leg extensions 34, 38 between the open and the closed positions. In one embodiment, the thickness of actuator 66 may be uniformly increasing or decreasing, or have alternate diameter dimensions along axis L1. In some embodiments, all or only a portion of surfaces of actuator 66 may have alternate surface configurations, such as, for example, those alternatives described herein. In one embodiment, actuator 66 may have alternate cross section configurations, such as, for example, oval, oblong, triangular, rectangular, square, polygonal, irregular, uniform, non-uniform, variable and/or tapered.

Actuator 66 includes an elongated portion 68 and a distal head 70. Elongated portion 68 includes walls 72 that have a generally uniform configuration for slidable engagement with walls 56, 58. Distal head 70 is enlarged relative to elongated portion 68 and tapers distally to an increased width. Elongated portion 68 includes an aperture 73 that receives a pin 74 for connecting actuator 66 with lock 100, as discussed herein. Lock 100 is configured for manipulation to facilitate and prevent axial movement of actuator 66 and thereby cause leg extensions 34, 38 to move or prevent movement thereof.

As the tapered configuration of distal head 70 slides along surfaces 45, 53, engagement of their respective surfaces causes reciprocal and complimentary motion in leg extensions 34, 38 such that distal engagement parts 36, 40 move in a direction transverse to axis L1 between the closed position and the opened position such that distal engagement parts 36, 40 are in an open state. In the closed state, engagement parts 36, 40 releasably capture an implant.

Distal head 70 includes an aperture 76 that receives a pin 78 for connecting actuator 66 with leg extensions 34, 38. Pin 78 engages a part 80 that is configured for disposal in a slot 79 formed in distal head 70. Part 80 includes a dog bone configuration with enlarged end portions 82. Enlarged end portions 82 are tapered and are configured to slidably engage slots 42, 50 of leg extensions 34, 38. Enlarged end portions 82 are configured to slide along tapered track surfaces 44, 52 such that engagement of their respective surfaces causes reciprocal and complimentary motion in leg extensions 34, 38 and distal engagement parts 36, 40. As such, slots 42, 50 are configured to allow and limit movement of actuator 66 and facilitate retention of distal engagement parts 36, 40 in the open and closed positions.

A sleeve 84 is configured for slidable disposal about portion 14. Sleeve 84 is configured to engage actuator 66 via pin 74. Sleeve 84 includes an inner surface 86 that defines passageway 88. Passageway 88 is configured to receive portion 14. In some embodiments, all or only a portion of surface 86 may have alternate surface configurations, such as, for example, rough, threaded for connection with surgical instruments, arcuate, undulating, porous, semi-porous, dimpled, polished and/or textured according to the requirements of a particular application.

Figure 9:
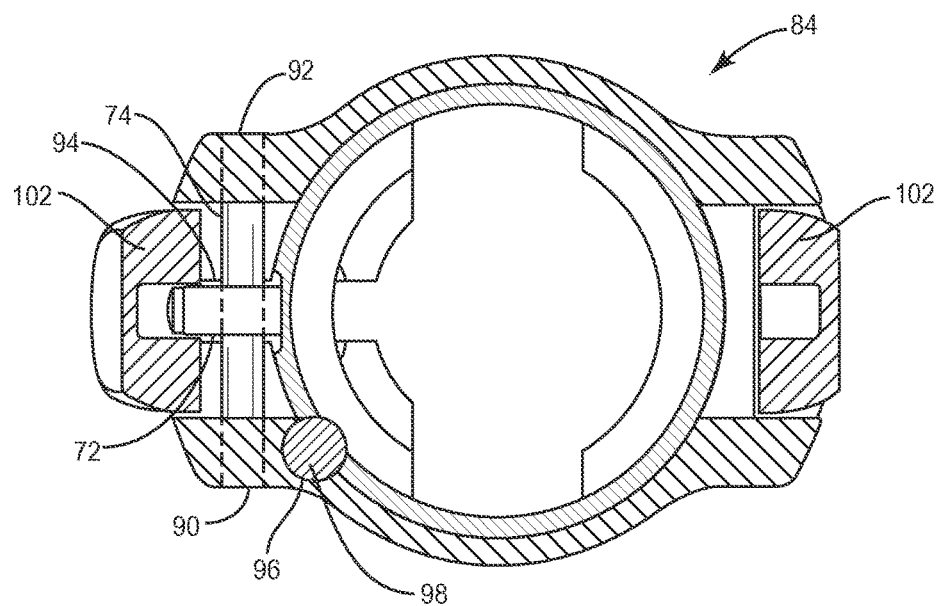
FIG. 9 is an axial view of components of the system shown in FIG. 1.
Figure 11:
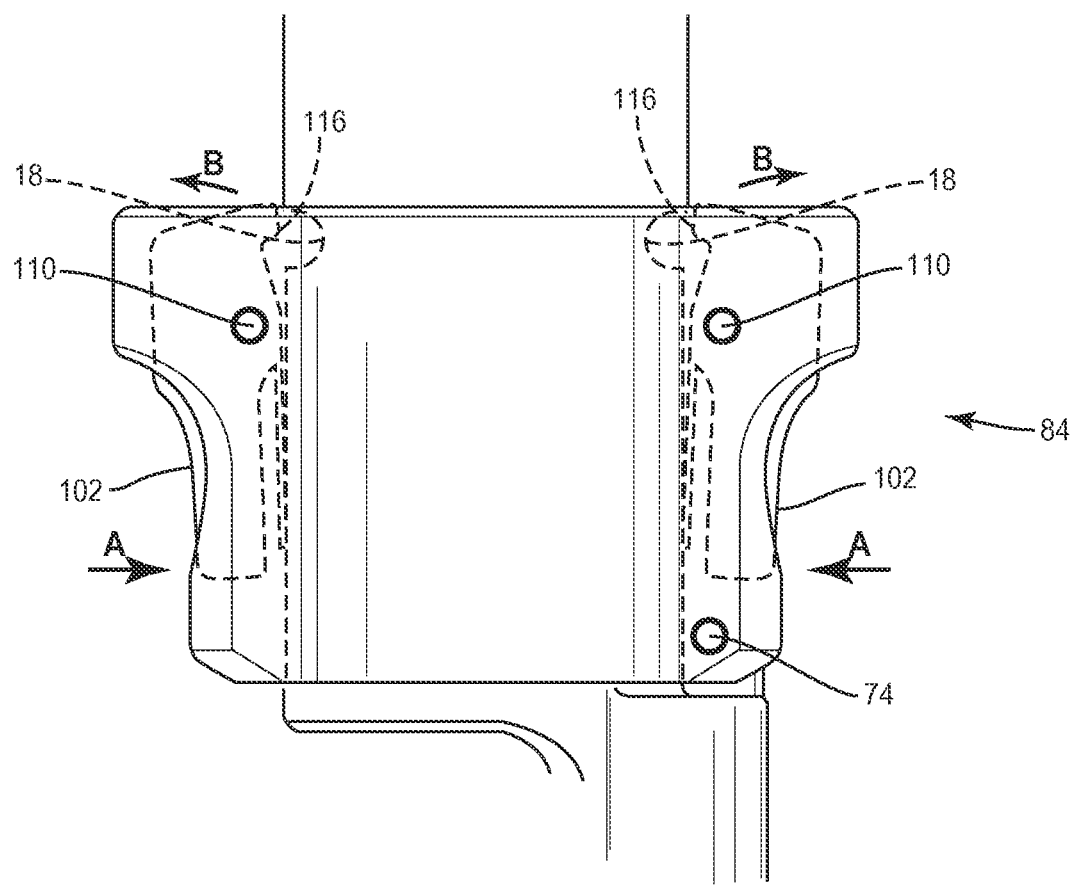
FIG. 11 is a side view of components of the system shown in FIG. 1.

As shown in FIGS. 9 and 11, surface 86 defines cavities 90, 92 and slot 94. Actuator 66 is configured for disposal in slot 94. Cavities 90, 92 are configured to receive pin 74. Pin 74 extends through cavity 90, through aperture 72 of actuator 66 and through cavity 92. Translation of sleeve 84 along portion 14 engages actuator 66 thereby engaging extensions 34, 38. In one embodiment, sleeve 84 includes a guide cavity 96 configured to receive a guide member, such as, for example, a pin 98. Pin 98 extends along axis L1 and is disposed with arm 16. Pin 98 is configured to facilitate axial translation of sleeve 84 as it translates along portion 14 and prevents rotation of sleeve 84. In some embodiments, all or only a portion of a surface of pin 98 may have alternate surface configurations, such as, for example, rough, threaded for connection with surgical instruments, arcuate, undulating, porous, semi-porous, dimpled, polished and/or textured according to facilitate engagement with cavity 96 of sleeve 84.

Figure 3:
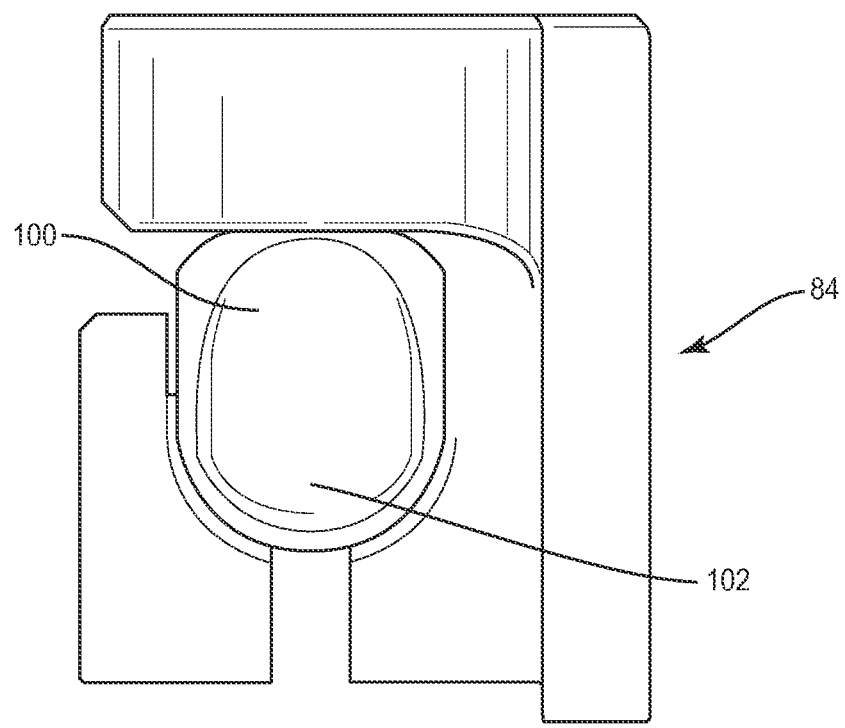
FIG. 3 is a side view of components of the system shown in FIG. 1.
Figure 4:
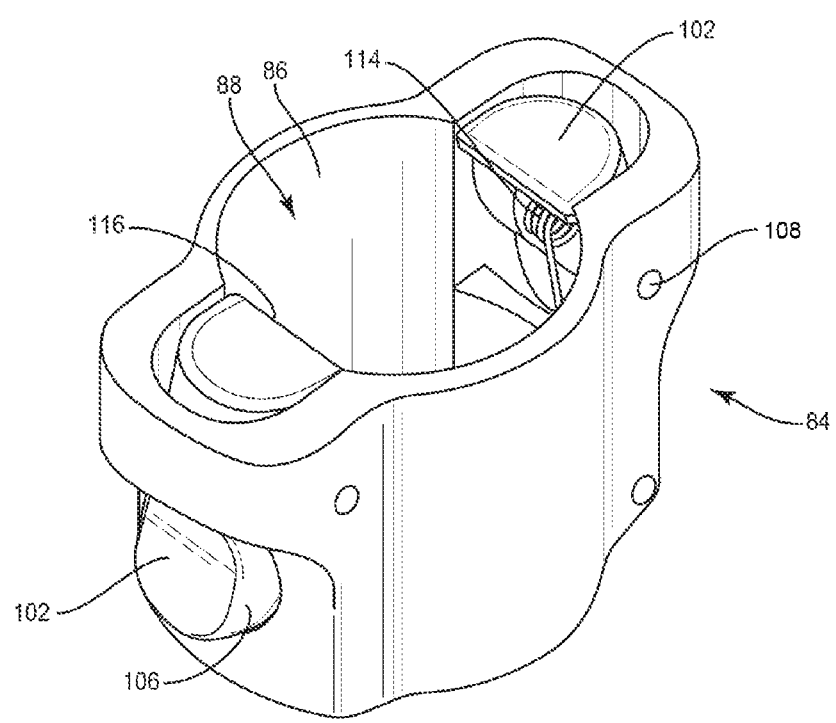
FIG. 4 is a perspective view of components of the system shown in FIG. 1.
Figure 5:
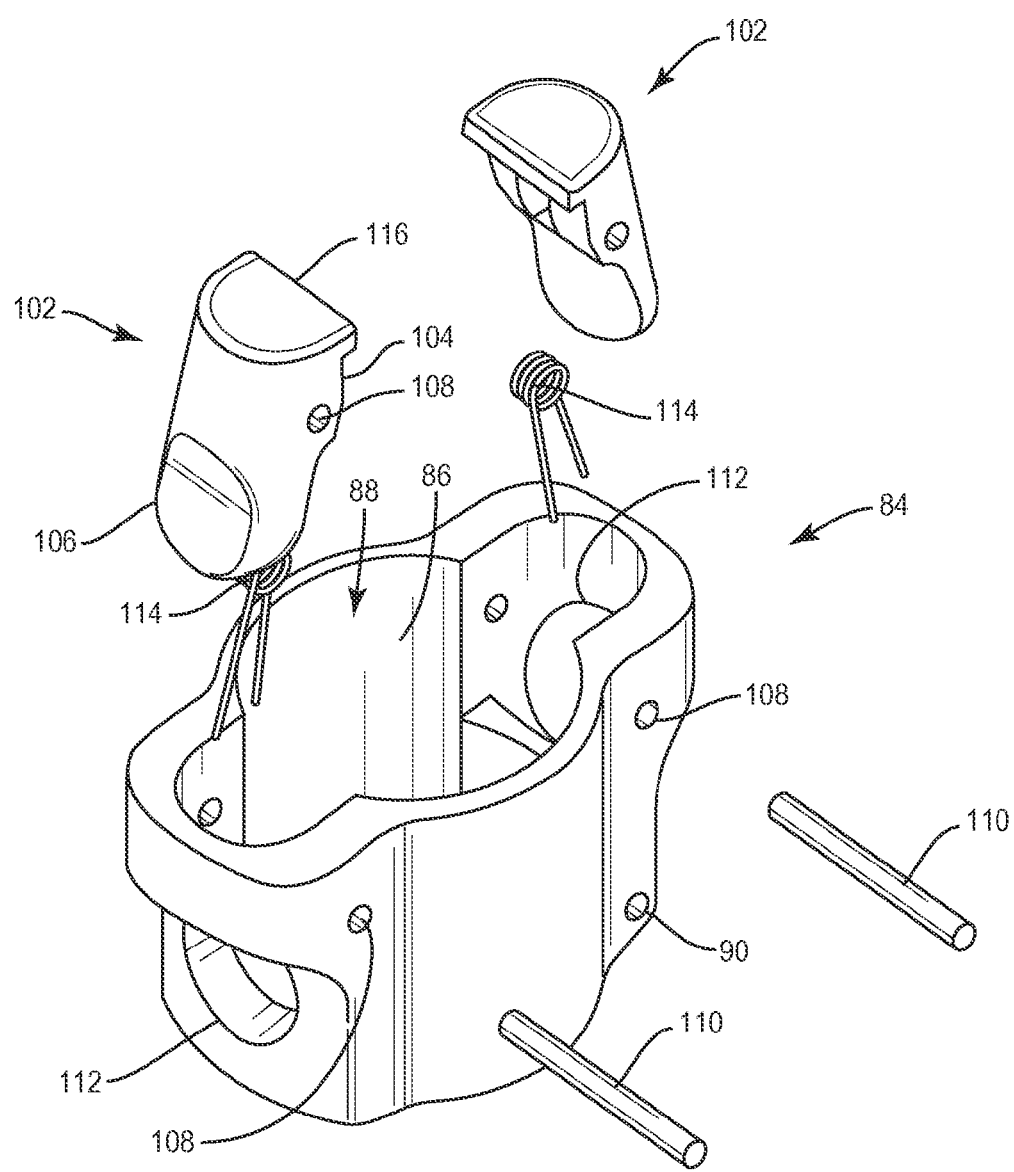
FIG. 5 is a perspective view of components of the system shown in FIG. 1 with parts separated.

As shown in FIG. 3, sleeve 84 includes a lock 100 configured for disposal between a first configuration and a second configuration and resists disengagement of arm 16 from the second position. Lock 100 includes at least one pivoting member, such as, for example, a rotatable button 102. In one embodiment, as shown in FIGS. 1-4, lock 100 includes a pair of buttons 102 having the same configuration. Each button 102 includes an inner surface 104 and an outer surface 106. Surface 104 defines a transverse channel 108. Each channel 108 is configured for engagement with a pin 110 to connect button 102 within a recess 112 defined within sleeve 84. Pin 110 is configured to facilitate pivoting of button 102 between the first configuration and the second configuration. Surface 106 defines a gripping surface configured to facilitate rotation of button 102 about pin 110. In some embodiments, all or only a portion of a surface 106 may have alternate surface configurations, such as, for example, rough, threaded for connection with surgical instruments, arcuate, undulating, porous, semi-porous, dimpled, polished and/or textured according to facilitate gripping.

Figure 10:
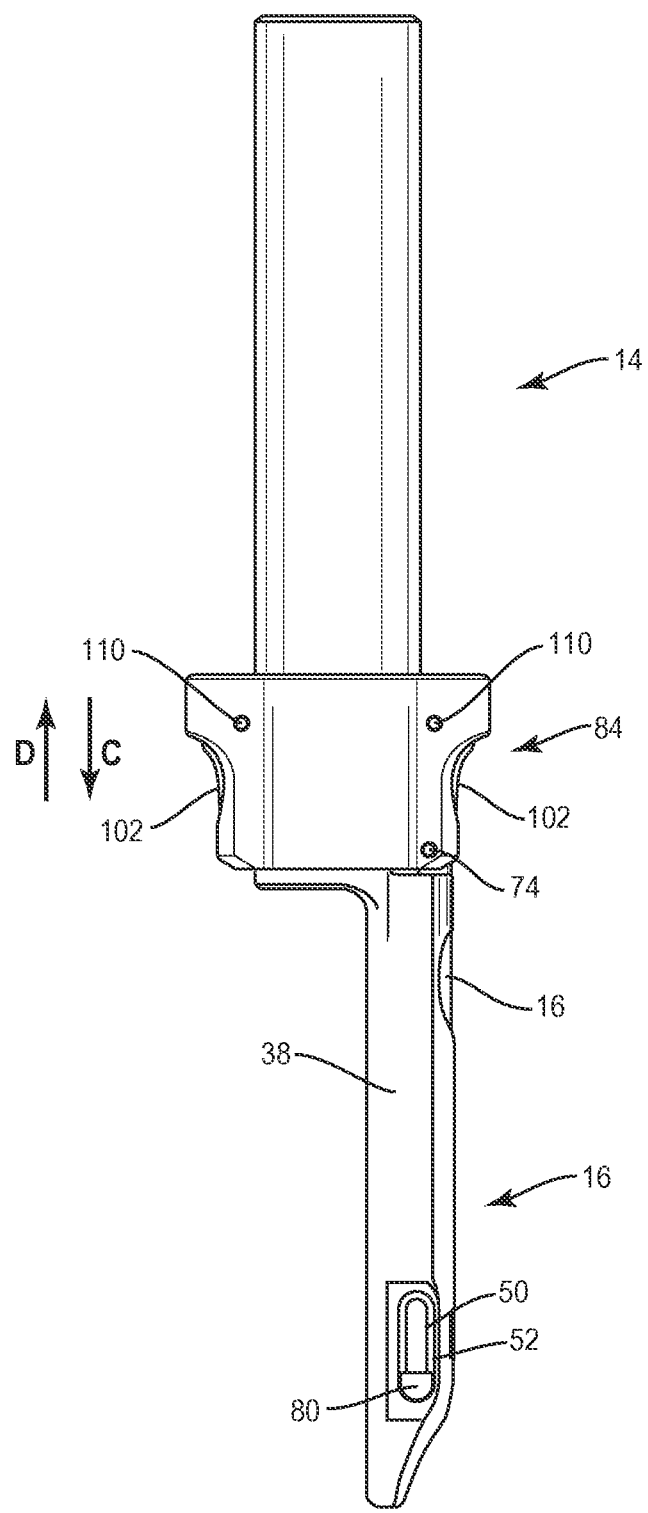
FIG. 10 is a side view of components of the system shown in FIG. 1.
Figure 12:
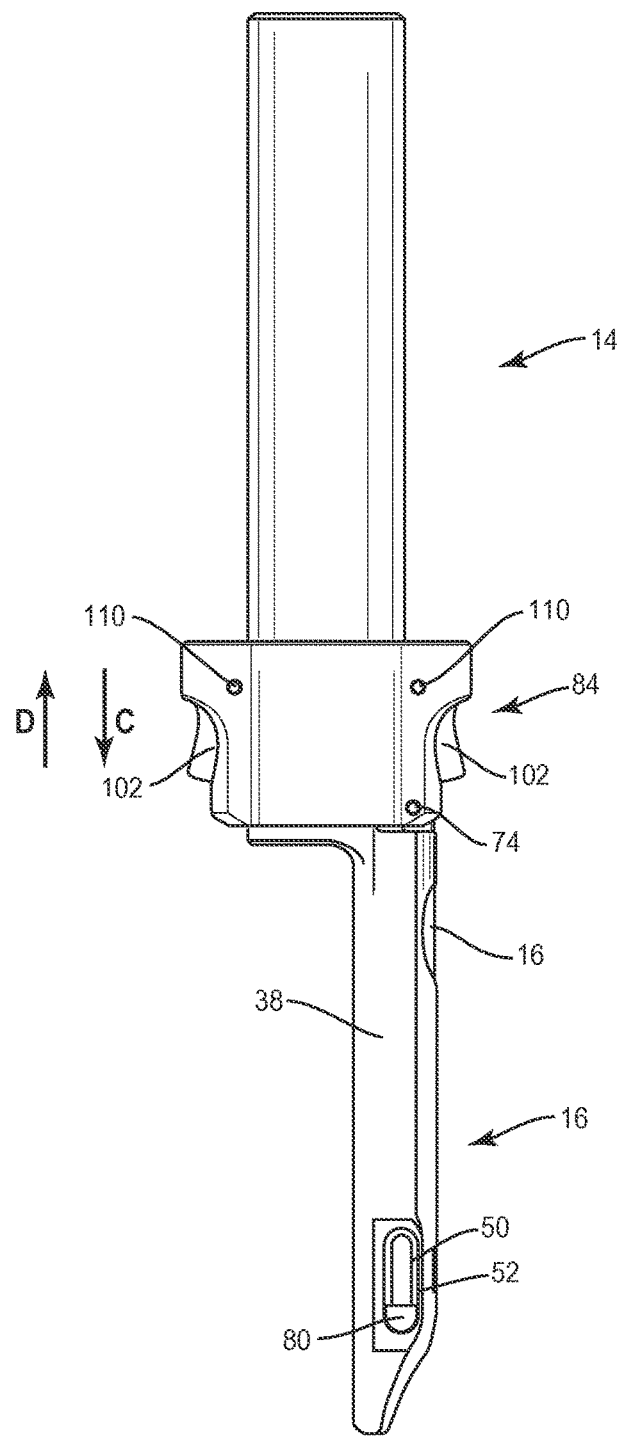
FIG. 12 is a side view of components of the system shown in FIG. 1.
Figure 13:
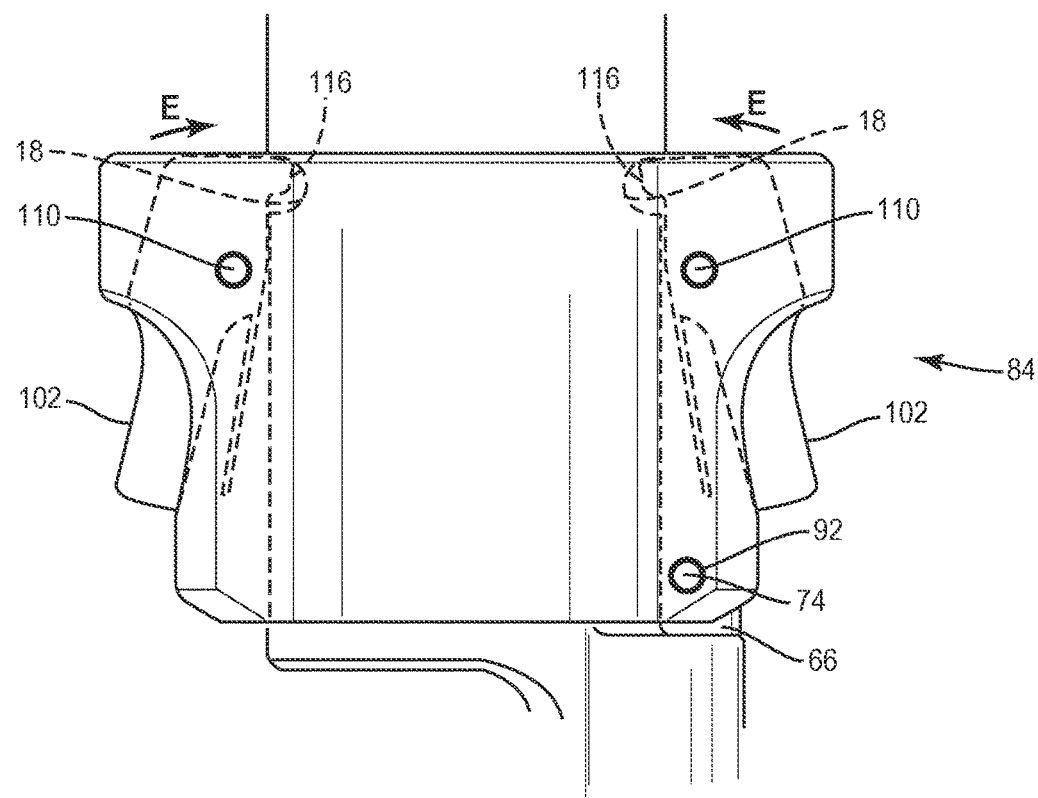
FIG. 13 is a side view of components of the system shown in FIG. 1.

Each button 102 includes a biasing member, such as, for example, a spring 114 configured to engage an underside of button 102 to bias button 102 between first and second configurations. Each button 102 includes a flange 116 extending transversely from surface 104. Flange 116 is configured to engage slot 18 to prevent translation of sleeve 84 and resist disengagement of arm 16 from the second position. As shown in FIGS. 10 and 11, when button 102 is depressed, providing a force to resist the force exerted by spring 114, flange 116 is disengaged from slot 18 allowing for translation of sleeve 84 along portion 14. As shown in FIGS. 12 and 13, when buttons 102 are in the biased, second configuration, flange 116 is engaged with slot 18 to prevent sleeve from translating along portion 14.

In operation, extender 12 is oriented for manipulation. Buttons 102 are depressed, in the direction shown by arrows A in FIG. 11, and buttons 102 rotate about pin 110, in the direction shown by arrows B in FIG. 11. Rotation of button 102 causes flange 116 to rotate away from surface 30 of portion 14 and disengage slot 18 such that sleeve 84 is translatable relative to and along portion 14, in the directions shown by arrows C and D in FIG. 10.

Figure 16:
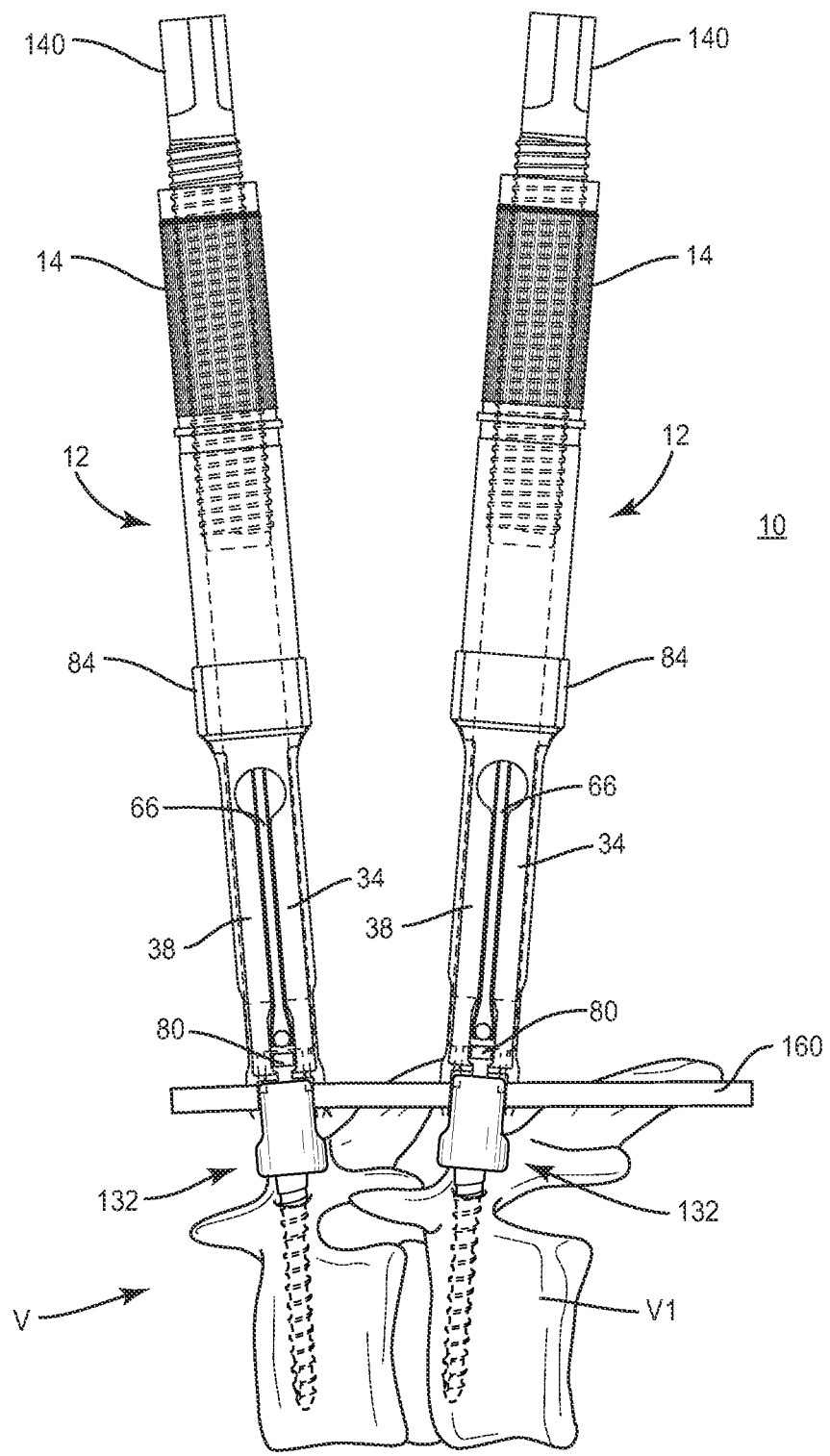
FIG. 16 is a side view of components of the system and vertebrae shown in FIG. 15.

As actuator 66 translates distally, distal head 70 slides along surfaces 45, 53 distally such that engagement of their respective surfaces causes reciprocal and complimentary motion in leg extensions 34, 38 in an inward direction transverse to axis L1 to engage fastener 132. Slots 42, 50 guide movement of actuator 66 via engagement with part 80. The proximal and distal ends of each of slots 42, 50 provide a movement limit for actuator 66 as part 80 translates up and down slots 42, 50. Actuator 66 is manipulated such that distal engagement parts 36, 40 are brought into close proximity with a head 133 of fastener 132. Protrusions 46, 54 are aligned with corresponding receiving cavities 134 of fastener 132, as shown in FIG. 16.

Extender 12 engages fastener 132 and buttons 102 are released such that buttons 102 are biased by springs 114 to rotate, in the direction shown by arrows E in FIG. 13. Rotation of button 102 causes flange 116 to engage slot 18, as shown in FIG. 13. Engagement of flange 116 with slot 18 provides resistance preventing sleeve 84 from migrating in a proximal direction. As such, actuator 66 is prevented from proximal translation thereby preventing part 80 from proximal movement that would cause protrusions 46, 54 of extensions 34, 38 to disengage from fastener 132. In the locked position, other instruments such as, for example, a reducer 140 and/or a spinal rod 180 can be introduced.

Figure 14:
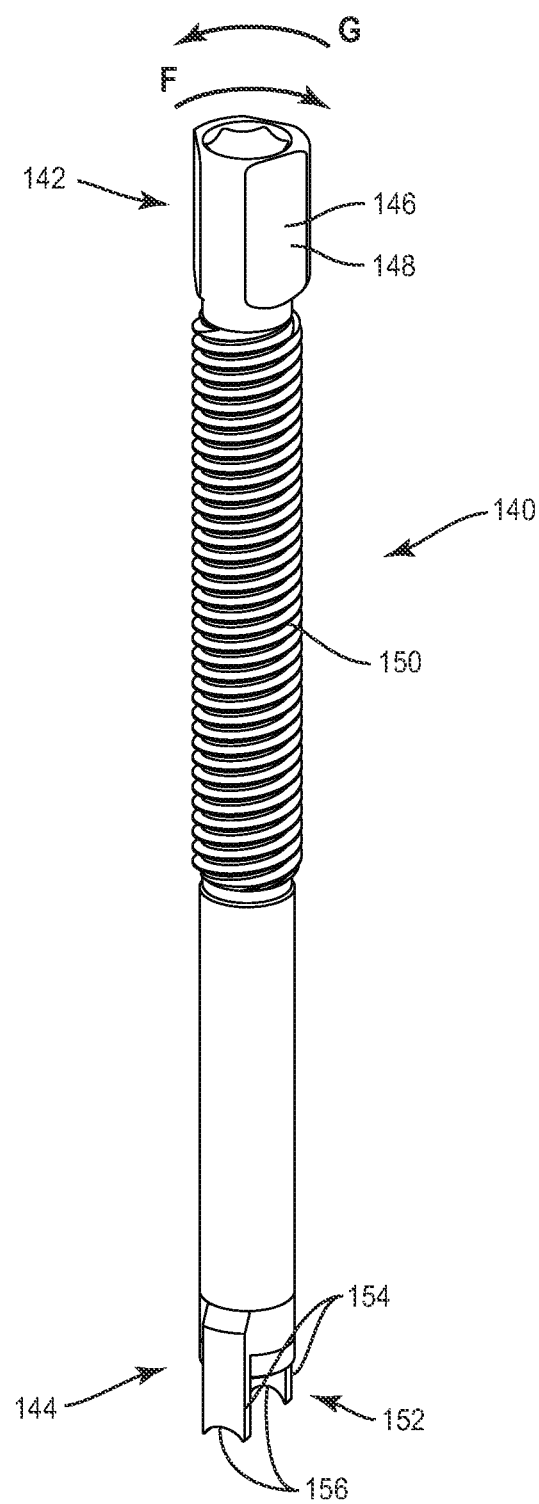
FIG. 14 is a perspective view of one embodiment of a component of a system in accordance with the principles of the present disclosure.

A reducer 140, as shown in FIG. 14, extends between a proximal end 142 and a distal end 144. Proximal end 142 includes a handle 146 having a grip surface 148. Handle 146 is manipulable to align reducer 140 with passageway 24. Reducer 140 is disposable in passageway 24 and defines an outer threaded surface 150. Handle 146 is rotated such that surface 150 engages threaded surface 26 to facilitate axial translation of reducer 140 relative to extender 12 along axis L1. Distal end 144 includes a pusher portion 152 that is engageable with a vertebral construct, such as, for example, a vertebral rod 160, as shown in FIG. 16. Rod 160 is configured for fixation with bone fastener 132. Pusher 152 includes legs 154 having arcuate end surfaces 156 configured to engage rod 160.

Upon positioning and fixation of bone fastener 132 within tissue at a surgical site and engagement with extender 12, threaded surface 150 is aligned with surface 26 of extender 12. Handle 146 is rotated, in the direction shown by arrow F in FIG. 14, to translate reducer 140 distally along axis L1 relative to extender 12. Reducer 140 is translated such that arcuate end surfaces 156 engage rod 160 in a configuration to reduce rod 160 into engagement with bone fastener 132. Reducer 140 is further translated to drive rod into a U-shaped head 133 of fastener 132 for fixation with bone fastener 130.

Handle 146 is rotatable, in the opposite direction shown by arrow G in FIG. 14, to translate reducer 140 proximally such that reducer 140 is removed from extender 12. Rod 160 can be fixedly secured with bone fastener 132 via a set screw (not shown) or similar securement. In one embodiment, the system may include one or a plurality of extenders, inserters, reducers, bone fasteners and/or vertebral constructs, which may be alternately sized and dimensioned, and arranged as a kit.

Figure 15:
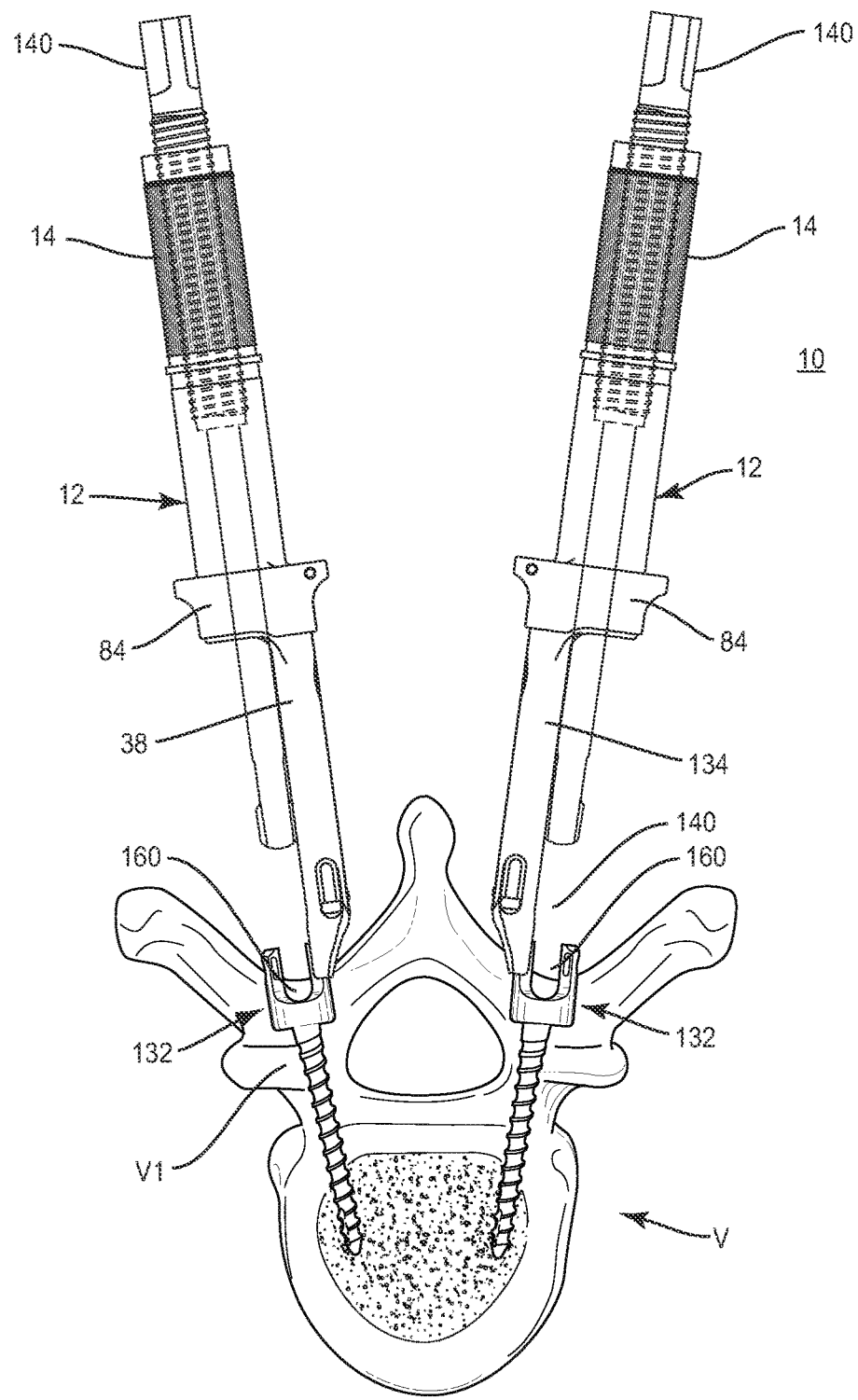
FIG. 15 is an axial view of components of one embodiment of a system in accordance with the principles of the present disclosure disposed with vertebrae.

In assembly, operation and use, system 10 is employed with a surgical procedure, in accordance with the principles of the present disclosure, for treatment of a spinal disorder affecting a section of a spine of a patient, as discussed herein. System 10 is employed with a surgical procedure for treatment of a condition or injury of an affected section of the spine including vertebrae V, as shown in FIGS. 15-16, to provide support and maximize stabilization of vertebrae V.

In use, to treat the affected section of the spine, a medical practitioner obtains access to a surgical site including vertebra V in any appropriate manner, such as through incision and retraction of tissues in an open or mini-open surgical technique. In one embodiment, system 10 may be used in any existing surgical method or technique including open surgery, mini-open surgery and minimally invasive surgery, whereby vertebrae V is accessed through a micro-incision, or sleeve that provides a protected passageway to the area. Once access to the surgical site is obtained, the particular surgical procedure is performed for treating the spinal disorder.

In one embodiment, system 10, described with regard to FIGS. 1-14, including extender 12, reducer 140, bone fastener 132 and/or a vertebral rod 170 is employed to augment the surgical treatment. For example, in one embodiment, system 10 delivers and introduces implants, such as, for example, bone fastener 132 and vertebral rod 160 at the surgical site including vertebra V. In one embodiment, the components of system 10 are configured to position vertebral rod 160 into engagement with bone fastener 132 for a correction treatment to treat adolescent idiopathic scoliosis and/or Scheuermann's kyphosis. In one embodiment, one or all of the components of system 10 can be delivered or implanted as a pre-assembled device or can be assembled in situ. System 10 may be completely or partially revised, removed or replaced.

Pilot holes (not shown) are made bilaterally in vertebrae V1 of vertebrae V for receiving bone fasteners 132. Extender 12 is oriented for manipulation with respect to fastener 132. Buttons 102 are depressed and rotate about pin 110. Rotation of buttons 102 cause flanges 116 to rotate away from surface 30 of portion 14 such that sleeve 84 is translatable relative to and along portion 14. As actuator 66 translates distally, distal head 70 slides along surfaces 45, 53 distally such that engagement of their respective surfaces causes reciprocal and complimentary motion in leg extensions 34, 38 in an inward direction transverse to longitudinal axis L1 to engage fastener 132. Slots 42, 50 guide movement of actuator 66 via engagement with part 80. The proximal and distal ends of each of slots 42, 50 provide a movement limit for actuator 66 as part 80 translates up and down slots 42, 50. Actuator 66 is manipulated such that distal engagement parts 36, 40 are brought into close proximity with a head 133 of fastener 132. Protrusions 46, 54 are aligned with corresponding receiving cavities 134 of fastener 132, as shown in FIG. 16.

Extender 12 is engaged with fastener 132 and buttons 102 are released such that buttons 102 are biased by springs 114 to rotate, in the direction shown by arrows E in FIG. 13. Rotation of buttons 102 cause flanges 116 to engage slot 18. Engagement of flange 116 with slot 18 provides resistance preventing sleeve 84 from migrating in a proximal direction. Locking of sleeve 84 prevents actuator 66 from proximally translating thereby preventing part 80 from proximal movement that would cause protrusions 46, 54 of extensions 34, 38 to disengage from fastener 132.

Upon positioning and fixation of bone fastener 132 within tissue at a surgical site and engagement with extender 12, threaded surface 150 is aligned with surface 26 of extender 12. Handle 146 is rotated to translate reducer 140 distally along axis L1 relative to extender 12. Reducer 140 is translated such that arcuate end surfaces 156 engage rod 160 in a configuration to move rod 160 into engagement with bone fastener 132. Reducer 140 is further translated to drive rod 160 into head 133 of fastener 132 for fixation with bone fastener 130.

Handle 146 is rotatable, in the opposite direction to translate reducer 140 proximally such that reducer 140 is removed from extender 12. Rod 160 can be fixedly secured with bone fastener 132 via a set screw (not shown) or similar securement. In one embodiment, system 10 may include one or a plurality of extenders, inserters, reducers, bone fasteners and/or vertebral constructs, which may be alternately sized and dimensioned, and arranged as a kit.

In one embodiment, system 10 may include fastening elements, which may include locking structure, for assembling, attaching or connecting the instruments. In one embodiment, the locking structure may include fastening elements such as, for example, clips, hooks, adhesives and/or flanges. The components of system 10 can be made of radiolucent materials such as polymers. Radiomarkers may be included for identification under x-ray, fluoroscopy, CT or other imaging techniques. In one embodiment, the use of microsurgical and image guided technologies may be employed to access, view and repair spinal deterioration or damage, with the aid of system 10.

In some embodiments, system 10 includes an agent, which may be disposed, packed, coated or layered within, on or about the components and/or surfaces of system 10. In some embodiments, the agent may include bone growth promoting material, such as, for example, bone graft to enhance fixation of the fixation elements with vertebrae V. The components of system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implanted components of system 10 are removed from the surgical site and the incision is closed.

Figure 17:
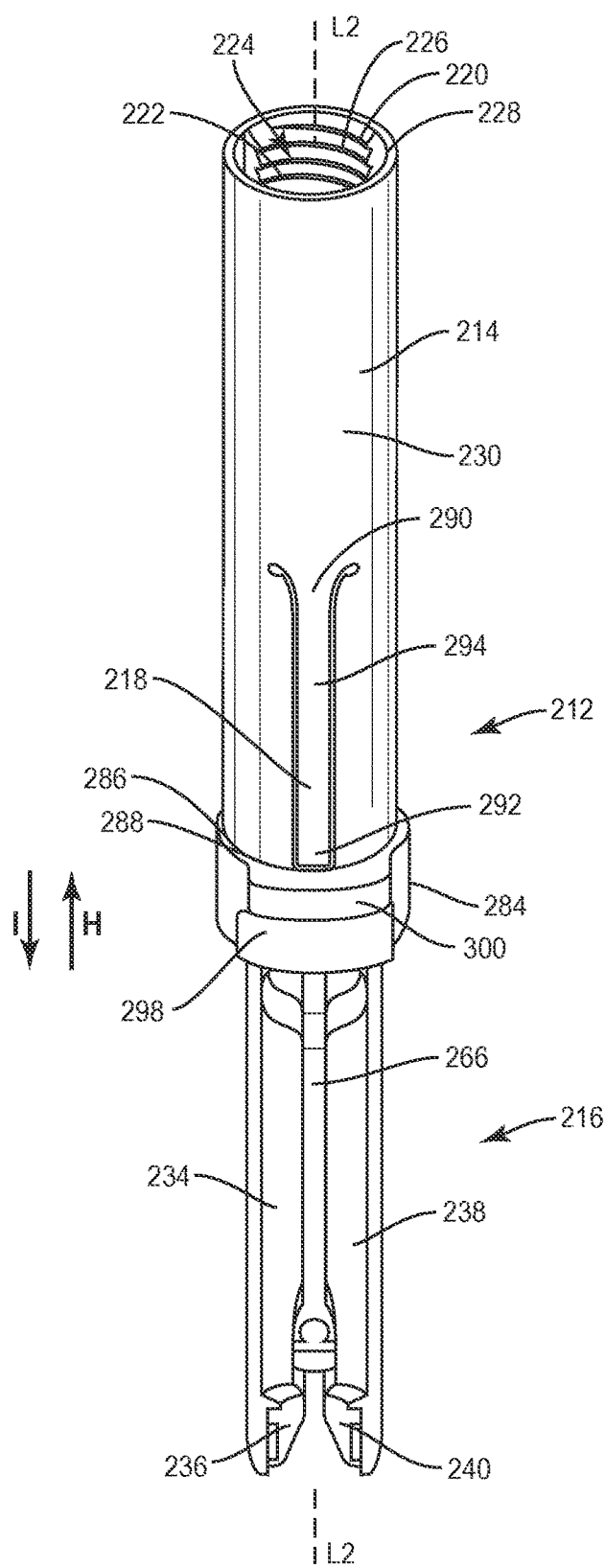
FIG. 17 is a perspective view of components of one embodiment of a system in accordance with the principles of the present disclosure.
Figure 18:
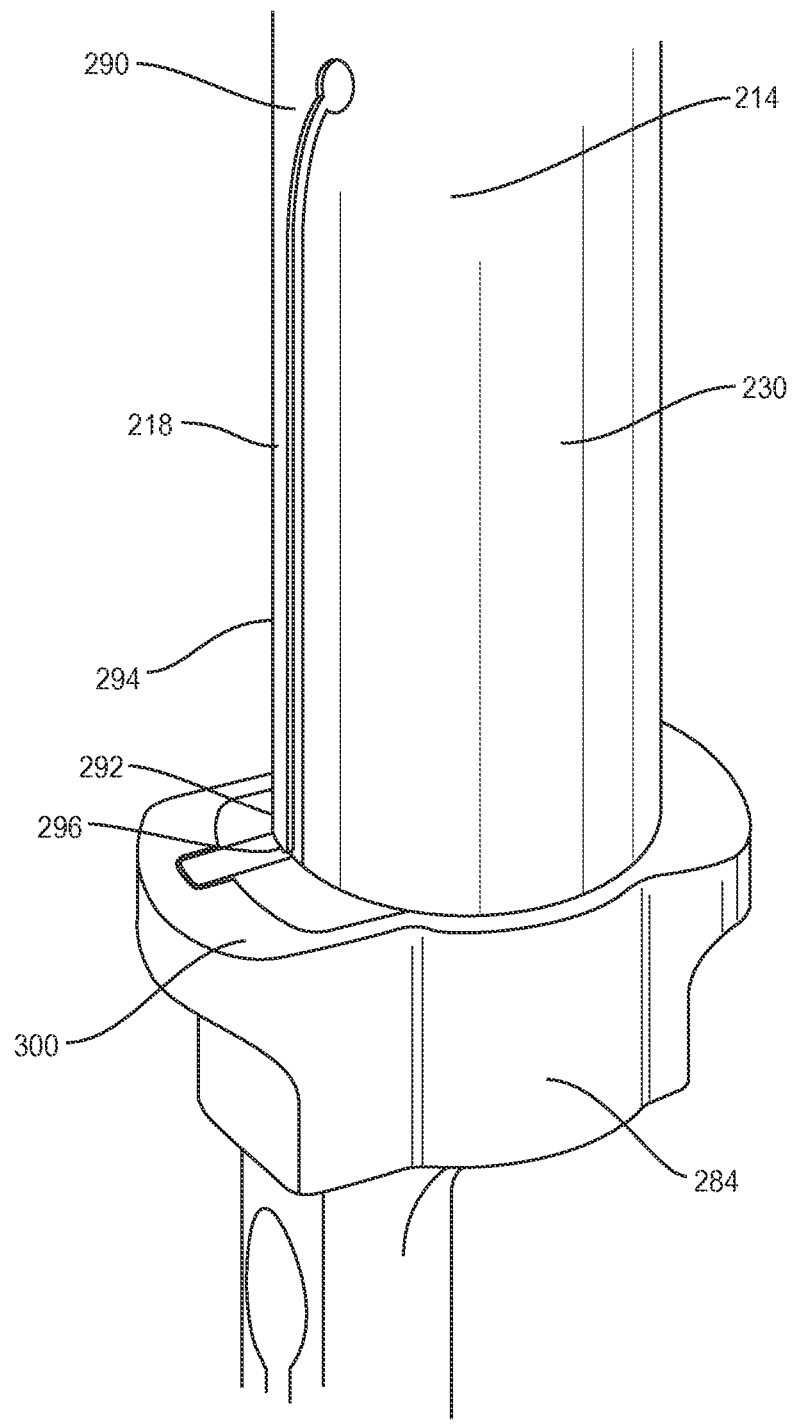
FIG. 18 is a perspective view of components of the system shown in FIG. 17.

In one embodiment, system 10, as shown in FIGS. 17-18, similar to the systems and methods described above with regard to FIGS. 1-16, includes an implant support, such as, for example, an extender 212, similar to extender 12 described herein. Extender 212 extends along a longitudinal axis L2 between a tubular portion 214 and an arm 216. Tubular portion 214 includes a cylindrical cross-section configuration and a proximal opening 220. Portion 214 includes an inner surface 222 that defines a passageway 224. Inner surface 222 includes a threaded portion 226 and a smooth, non-threaded portion 228. Portion 214 includes an outer surface 230 configured to for contact with a passageway 288 of sleeve 284, as discussed herein.

A lock, similar to those described herein, includes a portion of surface 230, which defines at least one cut-out, such as, for example, a resilient tab 218. Tab 218 is disposed with portion 214 and extends along axis L2. Tab 218 extends between an end 290 and an end 292 and includes an outer surface 294. End 292 includes an engagement surface 296 and is configured for biased engagement between a first configuration and a second configuration, as discussed herein. Tab 218 is resiliently biased such that in its initial state, a portion of surface 296 is in alignment with surface 230 and end 292 is deflected relative to surface 230 of portion 214. As the lock slides over end 292, end 292 is depressed and substantially all of surface 296 is in alignment with surface 230. As shown in FIG. 18, upon translation of the lock over end 292, tab 218 moves back to its initial deflected position such that end 292 extends outwardly relative to surface 230 and engagement surface 296 engages a flange of the lock, as discussed herein.

Arm 216, similar to arm 16 described above, extends along axis L2 and extends distally in a linear orientation from portion 214. Arm 216 includes a first movable leg extension 234 that defines a distal engagement part 236 and a second movable leg extension 238 that defines a distal engagement part 240.

An actuator 266, similar to actuator 66 described above, is configured for slidable disposal within extensions 234, 238. Actuator 266 is axially translatable to move leg extensions 234, 238 between the open and the closed positions.

The lock includes a sleeve 284 that is configured for slidable disposal about portion 214. Sleeve 284 is configured to engage actuator 266. Sleeve 284 includes an inner surface 286 that defines a passageway 288. Passageway 288 is configured to receive portion 214. Sleeve 284 includes an outer surface 298 that defines a gripping surface and a flange 300. Flange 300 extends transverse to axis L2. Flange 300 is configured for engagement with engagement surface 296 of tab 218 to lock sleeve 284 in the second configuration.

In one embodiment, flange 300 may extend in alternate configurations such as, for example, having a radius of curvature, offset and/or staggered, perpendicular and/or other angular orientations such as acute or obtuse, co-axial and/or parallel. In some embodiments, all or only a portion of surfaces 286, 298 may have alternate surface configurations, such as, for example, rough, threaded for connection with surgical instruments, arcuate, undulating, porous, semi-porous, dimpled, polished and/or textured according to enhance engagement. Translation of sleeve 284 relative to and along portion 214 and tab 218 causes sleeve 284 to depress tab 218. As sleeve 284 passes over end 292, tab 218 extends over flange 296 such that sleeve 284 is locked in the second position. Sleeve 284 engages actuator 266 thereby engaging extensions 234, 238 to translate along axis L2 and fixing extensions 234, 238 in a locked orientation.

In operation extender 212 is oriented for manipulation with respect to a bone fastener, similar to that described herein. Sleeve 284 is translatable relative to and along portion 214, in the directions shown by arrows H and I in FIG. 17. Translation of sleeve 284 causes sleeve 284 to apply a force to tab 218 to engage end 292 such that surface 294 aligns with surface 230. Sleeve 284 translates over end 292 and end 292 deflects back into its initial position such that engagement surface 296 engages flange 300 to lock sleeve 284 thereby locking extensions 234, 238 with a bone fastener.

Figure 19:
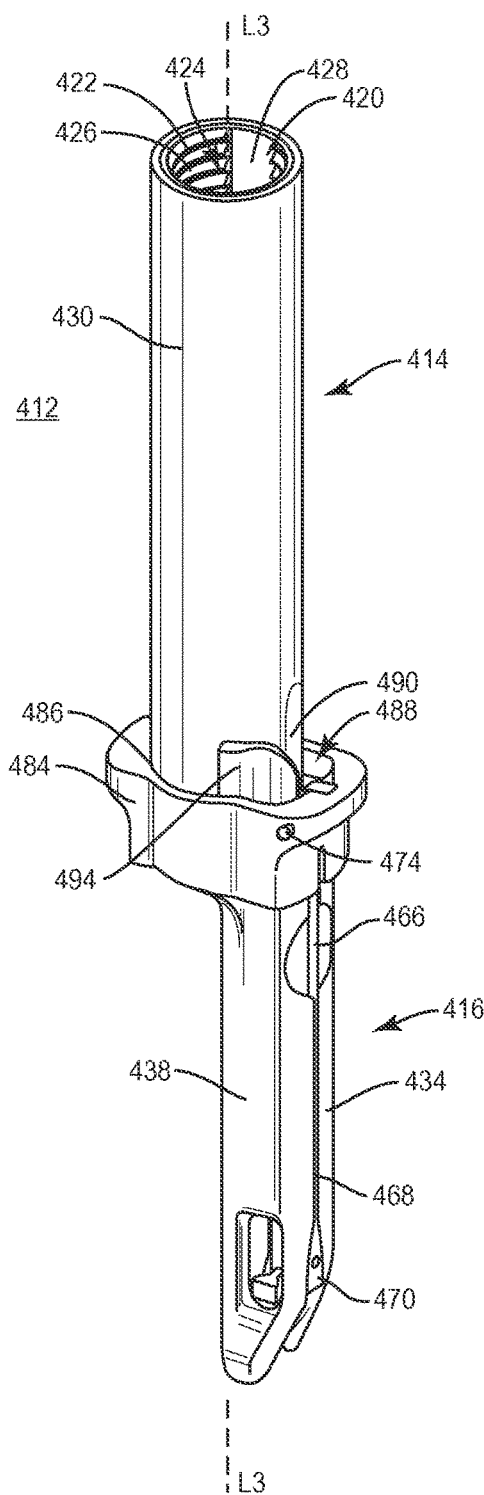
FIG. 19 is a perspective view of components of one embodiment of a system in accordance with the principles of the present disclosure.
Figure 20:
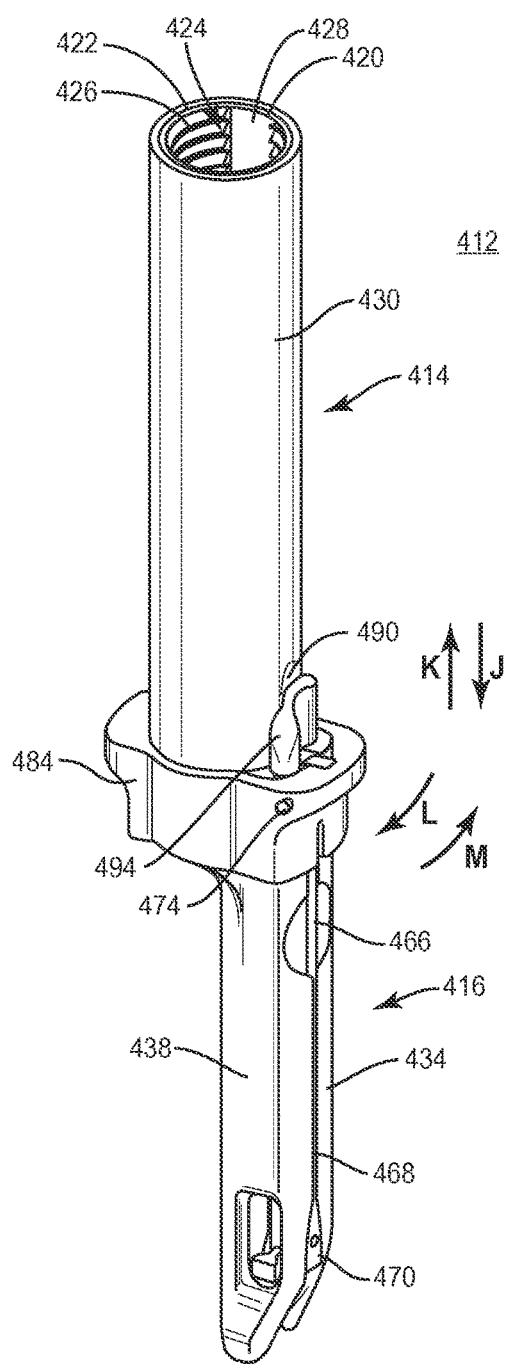
FIG. 20 is a perspective view of components of the system shown in FIG. 19.
Figure 21:
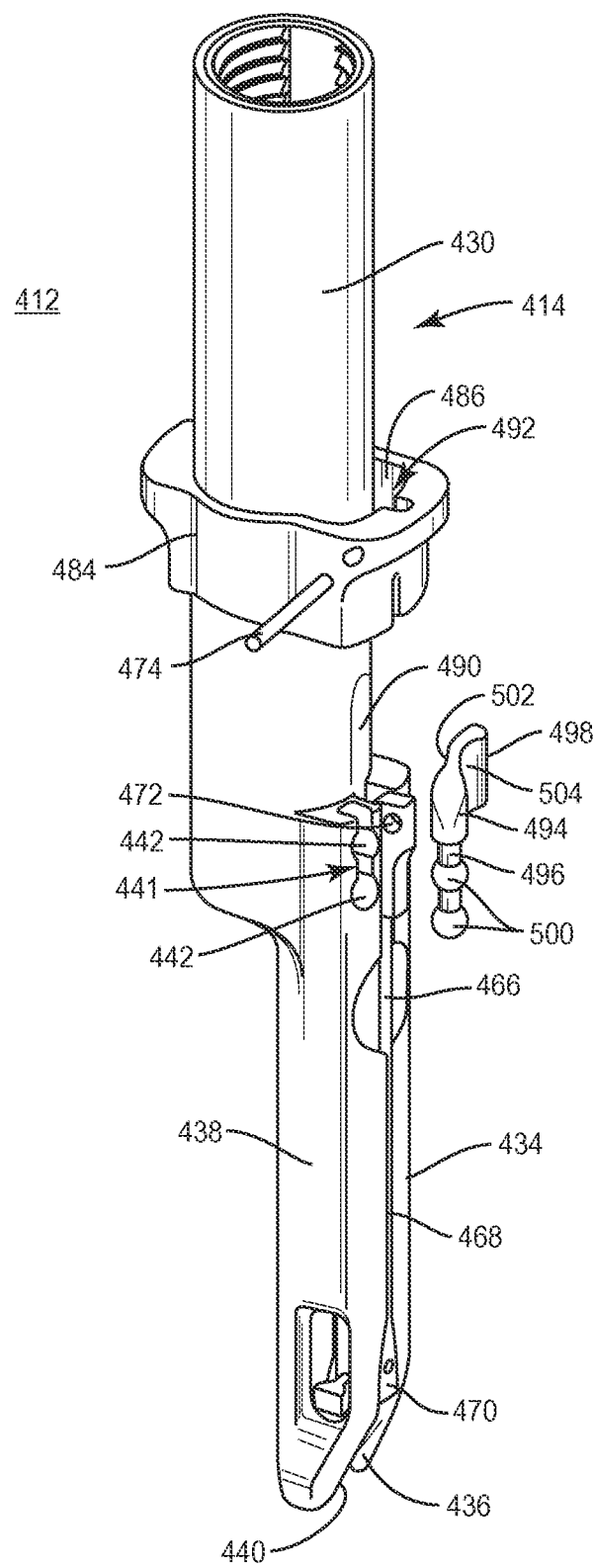
FIG. 21 is a perspective view of components of the system shown in FIG. 19 with parts separated.

In one embodiment, system 10, as shown in FIGS. 19-21, similar to the systems and methods described herein, includes an implant support, such as, for example, an extender 412, similar to extender 12 described herein. Extender 412 extends along a longitudinal axis L3 between a tubular portion 414 and an arm 416. Tubular portion 414 includes a cylindrical cross-section configuration and a proximal opening 420. Portion 414 includes an inner surface 422 that defines a passageway 424. Inner surface 422 includes a threaded portion 426 and a smooth, non-threaded portion 428. Portion 414 includes an outer surface 430 configured for contact with a passageway 488 of sleeve 484, as discussed herein. Surface 430 defines an indent 490 disposed at a distal end of portion 414. Indent 490 is configured to receive a lever 494, as discussed herein.

Arm 416, similar to arm 16 described above, extends along axis L3 and extends distally in a linear orientation from portion 414. Arm 416 includes a movable leg extension 434 that defines a distal engagement part 436 and a movable leg extension 438 that defines a distal engagement part 440. Arm 416 includes an axial cavity 441 including rounded cavities 442 configured for disposal of a portion of a lever, as discussed herein.

An actuator 466, similar to actuator 66 described above, is configured for slidable disposal within extensions 434, 438. Actuator 466 is axially movable to move leg extensions 434, 438 between the open and the closed positions. Actuator 466 includes an elongated portion 468 and a distal head 470. Elongated portion 468 includes an aperture 472 that receives a pin 474 for connecting actuator 466 with a lock, similar to those described herein. The lock is configured for manipulation to facilitate and prevent axial movement of actuator 466 and thereby facilitate movement of leg extensions 434, 438 or prevent movement thereof.

The lock including a sleeve 484 that is configured for slidable disposal about portion 414. Sleeve 484 is configured to engage actuator 466 via pin 474. Sleeve 484 includes an inner surface 486 that defines a passageway 488. Passageway 488 is configured to receive portion 414. Surface 486 defines a cavity 492 configured for disposal of a lever 494 of the lock. Lever 494 is rotatable to lock sleeve 484 between a first configuration and second configuration. Lever 494 includes an arm 496 and a flange portion 498. Arm 496 includes at least one rounded portion 500 configured to facilitate rotation of lever 494. Arm 496 is configured for disposal in axial cavity 441 and rounded portions 500 are configured for disposal in cavities 442. As shown in FIG. 21, flange 498 is arcuate in shape having a convex surface portion 502 and a concave surface portion 504. Portion 502 is configured for engagement with indent 490. Engagement of portion 502 with indent 490 allows for axial translation of sleeve 484. In the open position, portion 502 is engaged with indent 490 allowing for translation of sleeve 484. In the locked position, lever 494 is rotated in a direction transverse to axis L3 such that portion 502 is engaged with a portion of surface 430 and sleeve 484 causing a friction fit between lever 494 and surface 430 thereby preventing proximal axial translation of sleeve 484.

In one embodiment, flange 498 may extend in alternate configurations such as, for example, having a radius of curvature, offset and/or staggered, perpendicular and/or other angular orientations such as acute or obtuse, co-axial and/or parallel. In some embodiments, all or only a portion of surfaces 430, 502 may have alternate surface configurations, such as, for example, rough, threaded for connection with surgical instruments, arcuate, undulating, porous, semi-porous, dimpled, polished and/or textured according to enhance engagement.

In operation, similar to that described herein, sleeve 484 is configured for translation along portion 414, in the directions shown by arrows J and K in FIG. 20. Lever 494 is positioned such that portion 502 is in alignment with indent 492 thereby allowing translation of sleeve 484. Once extensions 434, 438 are engaged with a bone fastener, lever 494 is engaged. Lever 494 is rotated, in the direction shown by arrow L in FIG. 20, to lock sleeve 484. Rotation of lever 494 causes arm 496 and rounded portions 500 to rotate within axial cavity 441 and cavities 442 and portion 502 slide into engagement with surface 430.

Portion 502 is configured to apply a friction force against surface 430 such that proximal axial translation of sleeve 484 is prevented, thereby preventing migration of actuator 466 in a proximal direction and maintaining engagement of extensions 434, 438 with the bone fastener. To disengage extensions 434, 438 from the bone fastener, lever 494 is rotated, in the direction shown by arrow M in FIG. 20, to align portion 502 with indent 490 to allow proximal axial translation of sleeve 484 to disengage extensions 434, 438.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant support comprising:
   a first portion defining a longitudinal axis;
   a second portion including at least one arm extending from the first portion, the at least one arm including a part;
   an extension being engageable with the at least one arm to move the at least one arm between a first position and a second position such that the part is disposed to releasably engage an implant; and
   a lock disposed with the first portion and connected with the extension, the lock being biased from a first configuration to a second configuration to engage the first portion and resist disengagement of the at least one arm from the second position, the lock including a biasing member having a coiled body that extends transverse to the longitudinal axis, the biasing member being configured for engagement with the first portion to prevent the lock from disengaging the first portion,
   wherein the biasing member includes a first extension that extends from a first end of the coiled body and a second extension that extends from a second end of the coiled body.

2. An implant support as recited in claim 1, wherein the at least one arm includes a longitudinal guide member configured to support the lock.

3. An implant support as recited in claim 2, wherein the guide member facilitates axial translation of the lock relative to the first portion and is configured to prevent rotation of the lock relative to the first portion.

4. An implant support as recited in claim 1, wherein the at least one arm includes an axial slot configured for disposal of the extension such that translation of the extension along the axial slot limits movement of the at least one arm between the first position and the second position.

5. An implant support as recited in claim 1, wherein the at least one arm includes a first leg extension and a second leg extension, the leg extensions defining an axial slot configured for relative movement of the extension.

6. An implant support as recited in claim 1, wherein the lock includes at least one pivoting member biased for rotation to the second configuration.

7. An implant support as recited in claim 1, wherein the lock includes at least one rotatable button biased for rotation, the at least one rotatable button includes a flange engageable with a slot of the first portion.

8. An implant support as recited in claim 7, wherein the at least one button is spring biased between the first configuration and the second configuration.

9. An implant support as recited in claim 1, wherein the lock includes at least one rotatable button spring biased between the first configuration and the second configuration, the button having a flange engageable with a slot of the first portion.

10. An implant support as recited in claim 1, wherein the biasing member is a spring.

11. An implant support as recited in claim 1, wherein the biasing member is a torsion spring.

12. An implant support as recited in claim 1, wherein the lock includes a sleeve, a button that is rotatable relative to the sleeve, and a pin that extends through the sleeve, the coiled body and the button.

13. An implant support as recited in claim 1, wherein the biasing member comprises spaced apart springs, the lock including a sleeve, buttons that are each rotatable relative to the sleeve, and pins that each extend through the sleeve and one of the buttons.

14. An implant support as recited in claim 13, wherein the pins each extend through the coiled body of one of the springs.

15. An implant support as recited in claim 1, wherein the at least one arm includes a first leg extension and a second leg extension, the leg extensions defining an axial slot configured for relative movement of the extension, the leg extensions each extending from a proximal end surface to a distal end surface, the first portion comprising a longitudinal guide member configured to support the lock, the longitudinal guide member comprising a cylindrical pin that extends from one of the proximal end surfaces.

16. An implant support as recited in claim 15, wherein the pin is positioned in a guide cavity that extends through one of the proximal end surfaces.

17. An implant support comprising:
   a first portion defining a longitudinal axis;
   a second portion including at least one arm extending from the first portion, the at least one arm including a part;
   an extension being engageable with the at least one arm to move the at least one arm between a first position and a second position such that the part is disposed to releasably engage an implant; and
   a lock disposed with the first portion and connected with the extension, the lock being biased from a first configuration to a second configuration to engage the first portion and resist disengagement of the at least one arm from the second position, the lock including a biasing member having a coiled body that extends transverse to the longitudinal axis, the biasing member being configured for engagement with the first portion to prevent the lock from disengaging the first portion, wherein the lock includes a sleeve, a button that is rotatable relative to the sleeve, and a pin that extends through the sleeve, the coiled body and the button.

18. An implant support as recited in claim 17, wherein the at least one arm includes a longitudinal guide member configured to support the lock.

19. An implant support comprising:

a first portion defining a longitudinal axis;

a second portion including at least one arm extending from the first portion, the at least one arm including a part;

an extension being engageable with the at least one arm to move the at least one arm between a first position and a second position such that the part is disposed to releasably engage an implant; and a lock disposed with the first portion and connected with the extension, the lock being biased from a first configuration to a second configuration to engage the first portion and resist disengagement of the at least one arm from the second position, the lock including a biasing member having a coiled body that extends transverse to the longitudinal axis, the biasing member being configured for engagement with the first portion to prevent the lock from disengaging the first portion, wherein the biasing member comprises spaced apart springs, the lock including a sleeve, buttons that are each rotatable relative to the sleeve, and pins that each extend through the sleeve and one of the buttons, and wherein the pins each extend through the coiled body of one of the springs.

20. An implant support as recited in claim 19, wherein the at least one arm includes a longitudinal guide member configured to support the lock.

* * * * *

UNITED STATES PATENT AND TRADEMARK OFFICE
CERTIFICATE OF CORRECTION

PATENT NO. : 9,918,753 B2  
APPLICATION NO. : 13/965949  
DATED : March 20, 2018  
INVENTOR(S) : May et al.

Page 1 of 1

It is certified that error appears in the above-identified patent and that said Letters Patent is hereby corrected as shown below:

In Column 13, Lines 10-11, delete "indent 492" and insert -- indent 490 --, therefor.

Signed and Sealed this  
Thirty-first Day of July, 2018

Andrei Iancu  
*Director of the United States Patent and Trademark Office*